United States Patent
Turner et al.

(10) Patent No.: US 9,879,303 B2
(45) Date of Patent: *Jan. 30, 2018

(54) CHROMOGENIC GLUCURONIDASE SUBSTRATES AND USES

(71) Applicant: Glycosynth Limited, Warrington cheshire (GB)

(72) Inventors: Hayley Jane Turner, Warrington cheshire (GB); Michael Burton, Warrington cheshire (GB)

(73) Assignee: GLYCOSYNTH LIMITED (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/035,136

(22) PCT Filed: Nov. 3, 2014

(86) PCT No.: PCT/GB2014/053259
§ 371 (c)(1),
(2) Date: May 6, 2016

(87) PCT Pub. No.: WO2015/067926
PCT Pub. Date: May 14, 2015

(65) Prior Publication Data
US 2016/0281127 A1    Sep. 29, 2016

(30) Foreign Application Priority Data

Nov. 8, 2013  (GB) .................................. 1319767.8

(51) Int. Cl.
| | | |
|---|---|---|
| *C12Q 1/34* | (2006.01) | |
| *C07H 15/20* | (2006.01) | |
| *C07H 15/203* | (2006.01) | |
| *G01N 33/569* | (2006.01) | |

(52) U.S. Cl.
CPC ............. *C12Q 1/34* (2013.01); *C07H 15/20* (2013.01); *C07H 15/203* (2013.01); *G01N 33/56911* (2013.01); *G01N 2333/924* (2013.01); *G01N 2333/942* (2013.01)

(58) Field of Classification Search
CPC ........ C07H 15/20; C07H 15/203; C12Q 1/34; G01N 2333/924; G01N 2333/942; G01N 33/56911
See application file for complete search history.

(56) References Cited

U.S. PATENT DOCUMENTS

| | | | |
|---|---|---|---|
| 6,534,637 B2 | 3/2003 | Shen et al. | |
| 8,216,802 B2 | 7/2012 | Casse et al. | |
| 2007/0065894 A1* | 3/2007 | Croteau | B01L 3/5085 435/18 |

FOREIGN PATENT DOCUMENTS

| | | |
|---|---|---|
| EP | 1438423 | 7/2004 |
| WO | 2012168415 | 12/2012 |

OTHER PUBLICATIONS

Rennick et al. Am. J. Physiol. (1970) 218(5): 1307-1312.*
McNabb et al. J. Comparative Physiol. (1973) 82: 47-57.*
McDonald et al. J. Agric. Food Chem. (1996) 44: 599-606.*
Luukkanen et al., "Enzyme-assisted synthesis and structural characterization of nitrocategchol glucuronides," Bioconjugate Chemistry, Jan. 1, 1999, 10: 150-154.
Olstadt et al., "A comparison of ten USEPA approved total coliform/ *E.coli* tests," Journal of Water and Health, Jan. 1, 2007, 5(2):267-282.
International Search Report and Written Opinion for PCT/GB2014/053259 dated Dec. 4, 2014.
Bhowmik, et al., A novel "pro-sensitizer" based sensing of enzymes using Tb(III) luminescence in a hydrogel matrix, Chem. Commun., 48, 4624-4626, (2012).
Bollenback, G.N. et al, J. Am. Chem. Soc., 77, 3310, (1955).
Brenner, K.P. et al, New medium for the simultaneous detection of total coliforms and *Escherichia coli* in water, Appl. Environ. Microbiol., 59, 3534-3544, (1993).
Costa et al., Modifications in the metabolic pathways of benzene in strptozotocin-induced diabetic rat, Arch Toxicol, 73, 301-306 (1999).
James, A.L. et al, Detection of specific bacterial enzymes by high contrast metal chelate formation. Part I. 8-Hydroxyquinoline-beta-D-glucoside, an alternative to aesculin in the differentiation of members of the family Enterobacteriaceae, Zentralbl. Bakteriol. Mikrobiol. Hyg. A, 267, 188, (1987).
Levvy, et al in Glucuronic Acid Free and Combined, Ed. G J Sutton Academic Press New York and London (1966) p. 317.
Perry, J.D. et al., Evaluation of novel chromogenic substrates for the detection of bacterial beta-glucosidase, J. Appl. Microbiol., 102, 410-415, (2007).
Reinders, R.D. et al, Use of 8-Hydroxyquinoline-β-d-glucuronide for presumptive identification of Shiga toxin-producing *Escherichia coli* O157,Lett. Appl. Microbiol., 30, 411-414, (2000).
Rompre, A. et al, Detection and enumeration of coliforms in drinking water: current methods and emerging approaches J. Microbial Methods, 49, 31-54, (2002).
Van der Hooft et al., Structural elucidation and quantification of phenolic conjugates present in human urine after tea intake, Analytical Chemistry (2012) 84(16) 7263-7271.

* cited by examiner

*Primary Examiner* — Susan Hanley
(74) *Attorney, Agent, or Firm* — Christopher M. Scherer; Daniel A. Blasiole; DeWitt Ross & Stevens S.C.

(57) ABSTRACT

Chromogenic substrates for β-D-glucuronidase activity comprising monoglucuronides of some 1,2-dihydroxyaromatic derivatives. When cleaved these form soluble colored conjugates with multivalent metal ions such as iron ions. The substrates may be used in conjunction with chromogenic substrates for other enzymes in microbial detection and identification especially involving liquid media. Microbes can be grown in the presence of the substrates and the compounds providing the metal ion. The substrates are particularly useful for detecting β-D-glucuronidase-positive *E. coli*. Synthetic methods for making the compounds are described.

9 Claims, No Drawings

US 9,879,303 B2

CHROMOGENIC GLUCURONIDASE SUBSTRATES AND USES

CROSS REFERENCE TO RELATED APPLICATIONS

The present application is the U.S. national stage application of International Application PCT/GB2014/053259, filed Nov. 3, 2014, which international application was published on May 14, 2015, as International Publication WO2015/067926. The International Application claims priority of British Patent Application 1319767.8, filed Nov. 8, 2013, the contents of which are incorporated herein by reference in their entireties.

FIELD OF USE

This invention relates to chromogenic enzyme substrates used to detect *E. coli* and other β-D-glucuronidase-producing microorganisms in liquid growth media.

BACKGROUND TO THE INVENTION

Rapid tests for the detection of *E. coli* are crucial in clinical laboratories and are important in monitoring the microbiological quality of food and water samples. The detection of *E. coli* and total coliforms in food and water samples is used as an indication of faecal contamination. The traditional methods used were based on membrane filtration and multiple-tube fermentation techniques. Increasingly in recent years, tests based on specific enzyme activities have been developed [A. Rompré et al, J. Microbial Methods, 49, 31-54, (2002)]. Several chromogenic and fluorogenic media have been developed that utilise β-D-glucuronidase activity as an indicator of *E. coli* and β-D-galactosidase activity for the simultaneous detection of total coliforms [J. Olstadt et al, J. Water and Health, 5, 287-282, (2007)]. These assays may be conducted in liquid media or on solid media such as agar plates. Some representatives among the many solid media commercially available that utilise this methodology serve as examples. C-EC Agar (Biolife Italiana Srl, Milan, Italy) uses fluorogenic MUG (4-methylumbelliferyl β-D-glucuronide) for the detection of *E. coli* and chromogenic X-Gal (5-bromo-4-chloro-3-indolyl β-D-galactopyranoside) for the detection of total coliforms. The MI-agar reported by Brenner and colleagues [K. P. Brenner et al, Appl. Environ. Microbiol., 59, 3534-3544, (1993)] employs chromogenic indoxyl β-D-glucuronide for the detection of *E. coli* and the fluorogenic substrate MUGAL (4-methylumbelliferyl β-D-galactopyranoside) for total coliforms. Coliscan® (Micrology LLC, Goshen, USA), Chromocult® Coliform agar (Merck, Darmstadt, Germany) and Chromogenic Coliform Agar (Biolife Italiana Srl, Milan, Italy) adopt a dual chromogenic system with the substrates X-β-D-glucuronide (5-bromo-4-chloro-3-indolyl β-D-glucuronide) [dark-blue to violet colour with *E. coli*] and 6-chloro-3-indolyl β-D-galactopyranoside [red colonies with other coliforms]. It will be noted that all of the above-mentioned media contain indoxyl substrates. Indoxyl substrates work very well in solid media such as agar plates, but they are much less suited to liquid media, mainly because the indigo chromogen they produce is very insoluble. In the few examples of liquid media for detecting *E. coli* and total coliforms which do contain an indoxyl substrate, it is a galactoside for the visualisation of total coliforms. Thus, Fluorocult® LMX broth and Readycult® Coliforms 100 (Merck, Darmstadt, Germany) as well as LSB X-Gal MUG (Biolife Italiana Srl, Milan, Italy) all incorporate MUG for the detection of *E. coli* and X-Gal for the detection of coliforms. Several commercially important liquid media for the *E. coli* total coliforms application rely on substrates that are not based on indoxyl. Colitag® (CPI International, Santa Rosa. USA) and ColiLert® (Idexx Laboratories, Westbrook, USA) media both utilise MUG (blue fluorescence) for the detection of *E. coli* and ONPG (o-nitrophenyl-β-D-galactopyranoside) (yellow colour) for the detection of coliforms. The Colisure® assay (Idexx Laboratories, Westbrook, USA) uses MUG and chlorophenol red-β-D-galactopyranoside (magenta colour) for the same purpose.

All of the media containing MUG suffer from the practical disadvantage that a fluorescence detector or, at the very least, a UV lamp is required to visualise the fluorescent endpoint following the hydrolysis of this substrate. It would therefore be a great advantage to have a chromogenic substrate capable of detecting β-D-glucuronidase activity from viable bacteria that is suitable for inclusion in a liquid medium, especially for use in combination with a substrate for β-D-galactosidase activity like ONPG. It therefore follows that the chromogenic substrate should not hinder bacterial growth and it should be suitable for continuous assays. Among other desirable properties it should be affordable, easy to use, and give a colour that is readily distinguished even in the presence of a different chromogen resulting from the hydrolysis of a β-D-galactosidase substrate. None of the currently available enzyme substrates for β-D-glucuronidase intended for use primarily in liquid media are suitable. For instance, PNP-β-D-glucuronide gives the same yellow colour as ONPG. Phenolphthalein-β-D-glucuronide is very expensive and the endpoint can only be visualised by adding alkali to raise the pH, thus introducing an extra step as well as stopping bacterial growth. Resorufin-β-D-glucuronide is another extremely expensive substrate, as is fluorescein-di-β-D-glucuronide. Methyl esters of glucuronides have been used as substrates for β-D-glucuronidase activity. Fluorescein-di-β-D-glucuronide dimethyl ester is a product of Marker Gene Technologies, Inc. (Eugene, Oreg., USA) [catalogue number M0969] and has been advertised as a β-D-glucuronidase substrate since 2004 [Marker Gene Technologies Newsletter, Vol. 4, Nos. 9 and 10, 2004]. The manufacturers state that this substrate has enhanced cell-permeation properties in plants. They have also advocated the substrate for routine coliform detection [Marker Gene Technologies Newsletter, Vol. 5, No. 3, 2005]. Application WO2012/168415 claims some cost advantages to using lower alkyl esters of glucuronides as substrates in place of the free acids or their salts, and exemplifies this with the use of resorufin-β-D-glucuronide methyl ester. The application WO2012/168415 states that the alkyl esters are not in themselves efficient substrates for β-D-glucuronidase, but work because the free acids are formed by in situ hydrolysis. Thus the resorufin-β-D-glucuronide-6-methyl ester was hydrolysed by β-D-glucuronidase less efficiently than resorufin-β-D-glucuronide free acid, especially in the absence of added esterase. Moreover, the core molecule resorufin is still very expensive. Chlorophenol red-β-D-glucuronide has been obtained in very poor yield only [G. G. Y. Shen et al, U.S. Pat. No. 6,534,637 (2003)]. This substrate was not incorporated into bacterial growth media; therefore its suitability to detect *E. coli* and total coliforms remains unknown. However, when Brenner and colleagues [K. P. Brenner et al, Appl. Environ. Microbiol., 59, 3534-3544, (1993)] combined the related compound chlorophenol red-β-D-galactopyranoside with indoxyl β-D-glucuronide in a dual chromogenic assay for *E. coli* and total coliforms on an agar plate medium, they found that there was not enough colour contrast between the different colonies. Therefore, it is by no means certain that chlorophenol red-β-D-glucuronide would be an effective substrate in this application in liquid or tube bacterial growth media, especially in combination with a different chromogenic substrate.

Mention should also be made of another expensive glucuronide substrate of limited commercial availability that has been used to detect *E. coli*, namely 8-hydroxyquinoline-β-D-glucuronide. When this substrate is cleaved the aglycone forms a highly insoluble intense black chelate with iron compounds [A. L. James and P. Yeoman, Zentralbl. Bakteriol. Mikrobiol. Hyg. A, 267, 188, (1987)]. Although the substrate has been demonstrated in an agar plate medium [R. D. Reinders et al, Lett. Appl. Microbiol., 30, 411-414, (2000)], toxicity of the aglycone to Gram-positive microbes has been observed [J. D. Perry et al, J. Appl. Microbiol., 102, 410-415, (2007)]. The substrate is not suitable for liquid media.

Enzyme substrates based on catechol have been described in EP1438423. However, this invention is restricted to chromogenic substrates giving a non-diffusible endpoint on solid media such as agar plates. Catechol-β-D-glucuronide is not disclosed in EP1438423. Although catechol-β-D-glucuronide has been mentioned occasionally in the scientific literature as a putative metabolic by-product from glucuronidation of either catechol or phenol, both the complete chemical synthesis and the characterisation of this glucuronide have yet to be described.

Bollenback and co-workers [G. N. Bollenback et al, J. Am. Chem. Soc., 77, 3310, (1955)] did prepare the fully protected precursor, catechol-2',3',4'-tetra-O-acetyl-β-D-glucuronide-6'-methyl ester, by chemical synthesis, but did not report deprotection of it to the free glycoside.

Maitra and Bhowmik [S. Bhowmik and U. Maitra, Chem. Commun., 2012, 46, 4624-4626] reported the use of 2,3-dihydroxynaphthalene-β-D-glucoside (DHN-β-D-glucoside) with terbium(III) in a luminescent assay for the detection of purified β-glucosidase. They make no mention of detecting microorganisms or of other glycoside derivatives of DHN.

Costa at al in Arch. Toxicol. (1999) 73:301-306 investigate metabolites derived from environmental benzene pollutant. The methodology subjects urine from rats fed with benzene to contact with β-glucuronidase, followed by analysis of the hydrolysis products by HPLC. Catechol is one of the hydrolysis products. The presence of a catechol glucuronide in the urine is assumed by inference. Costa et al do not isolate or characterise the catechol glucuronide. Costa at al do not provide any supporting evidence for the supporting structure, nor is there evidence for it being a a free glucuronide as opposed to an ester; esters are potential substrates for β-D-glucuronidase. Nor is there any evidence that the analyte that was hydrolysed was a mono-glucuronide, as opposed to a di-glucuronide. The use of β-glucuronidase to prove the structure of an analyte that is a substrate for the enzyme acknowledged in the art to be limited due to the lack of specificity of the enzyme. Thus β-glucuronidase hydrolyses other glycosides (Levvy at al in *Glucuronic Acid Free and Combined*, Ed. G J Sutton Academic Press New York and London 1966, page 317), so identifying a hydrolysis product is not conclusive proof that the starting substrate was even a glucuronide.

van der Hooft et al. in Analytical Chemistry (2012) 84(16) 7263-7271 identified pyrogallol-2-O-glucuronide as one compound present in quantities of less than 80 μmol in a complex mixture of metabolites in human urine after green tea intake. It was identified by mass spectrometry and ¹H-NMR spectra. As reported by van der Hooft, the structure of pyrogallol-2-O-glucuronide is ambiguous as the authors do not state whether the compound is the α- or the β-isomer.

SUMMARY OF THE INVENTION

This invention provides a method, compound, composition and synthesis for the detection of *E. coli* and other β-D-glucuronidase-producing microorganisms in liquid growth media.

According to a first aspect, the invention provides a method of detecting β-D-glucuronidase activity in a liquid medium comprising the steps of:

a) contacting a metal compound and a β-D-glucuronidase substrate according to the following formula I with a substance suspected of containing or producing a glucuronidase:

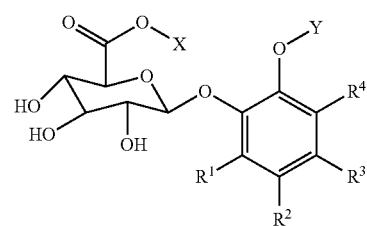

wherein X is independently selected from the group consisting of H, $CH_3$, $C_2$-$C_8$ alkyl, a metal cation or a non-metal cation;

wherein Y is independently selected from the group consisting of H, a metal cation, or a non-metal cation;

wherein either i) $R^1$ is H or OH and $R^4$ is H or $NO_2$; or ii) $R^1$ and $R^4$ are independently selected from the group consisting of H, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido; and wherein $R^2$ and $R^3$ are selected from the group consisting of H, OH, $C_1$-$C_8$ alkyl, $C_1$-$C_8$ alkoxy. $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_8$-$C_{24}$ aryl, sulfonyl and amido provided that $R^2$ and $R^3$ do not both represent OH, or $R^2$ and $R^3$ together form the group represented by the formula VI:

$$-CR^5=CR^6-CR^7=CR^8- \qquad VI;$$

wherein $R^5$-$R^8$ are independently selected from the group consisting of H, OH, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido provided that any vicinal groups $R^5$ to $R^8$ are not both OH;

such that a product of substrate cleavage is capable of chelating the metal compound, thereby forming a coloured compound; and b) detecting the presence of the coloured compound.

When $R^2$ and $R^3$ represent the said group VI, the group, together with the carbon atoms to which it is attached form a fused phenyl ring. The provisos excluding $R^2$ and $R^3$ and vicinal carbon atoms in group VI representing OH together means the substrate itself cannot complex the metal of the metal compound to form a coloured chelate.

The compound of the formula I is a substrate for β-D-glucuronidase, and is a glucuronide of an aromatic compound having two vicinal OH substituents in an aryl ring. The carboxylic acid group of the glucuronic unit may be in the form of the free acid (X is H) or may be esterified (X is alkyl) or may be in the form of a salt of an inorganic or organic base. In the latter case the carboxylic group is in the form of an anion, while X is a cation and the ions are electrostatically bound. Non-metal cations encompass inorganic cations, such as $NH^+_4$, and organic cations. An organic base is an ammonium compound e.g. a primary, secondary, tertiary or quaternary ammonium. An inorganic base is ammonium hydroxide or an oxide or hydroxide of an alkali metal, an alkaline earth metal or another metal $M^{n+}_{1/n}$ where n is 1, 2 or 3.

Preferably the compound of the formula I is a compound of the general formula II

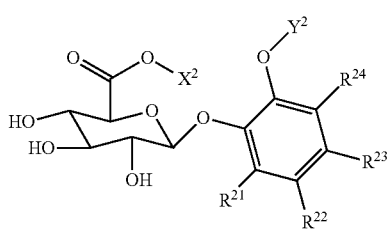

wherein $X^2$ is independently selected from the group consisting of H, $CH_3$, $C_2$-$C_6$ alkyl, a metal cation and a non-metal cation;

wherein $Y^2$ is independently selected from the group consisting of H, a metal cation and a non-metal cation;

wherein $R^{21}$ is H or OH;

wherein $R^{24}$ is H or $NO_2$; and wherein $R^{22}$ and $R^{23}$ are H or one of $R^{22}$ and $R^{23}$ is OH and the other is H, or $R^{22}$ and $R^{23}$ together form the group VII:

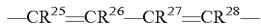

wherein $R^{25}$ to $R^{28}$ are independently selected from H, OH, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido, provided that any vicinal groups $R^{25}$-$R^{28}$ are not both OH.

The product of the glucuronidase cleavage comprises a diol compound having vicinal hydroxyl groups: this complexes metal ions, e.g. multivalent metal ions.

Some of the compounds of the formula II used in the first aspect are believed to be novel and form the second aspect of the invention.

According to a third aspect, the invention provides a composition comprising:

a) a compound represented by the formula I as defined above, preferably the formula II, as defined above; and b) a metal compound.

The composition may itself be a growth medium or may be a premix for adding to a growth medium, or a concentrate from which a growth medium, usually a liquid growth medium, may be formed, e.g. by dilution.

The metal compound may be a salt, preferably a water-soluble salt. The metal ion of the metal compound is one which forms a differently coloured complex with the diol cleavage product of the glucuronidase reaction compared to the glucuronide substrate. Preferred metal compounds are described below.

According to a fourth aspect, the invention provides a liquid medium composition suitable for the growth of microbes, preferably bacteria comprising:

a) a glucuronide of the formula I as defined above, preferably of the formula II as defined above; and b) a metal compound.

The liquid medium generally contains nutrients for microbial growth, growth promoters, growth inhibitors and/or substrates, preferably chromogenic substrates, for other microbial enzymes. We have found that the glucuronides defined herein and their cleavage products allow microbes to grow so that microbial growth can be carried out in the presence of those compounds. The metal compound is also selected for its compatibility with microbial growth. It is thus not necessary for either the substrate or metal compound to be added after a sample has been incubated such that putative enzyme activity is generated upon microbial growth. Rather the incubation medium can contain both compounds at the start of incubation.

According to a fifth aspect, the invention provides a concentrate, which upon dilution forms a liquid medium suitable for the growth of bacteria comprising:

a) a glucuronide of the formula I defined above, preferably formula II defined above; and b) a metal compound.

According to a sixth aspect, the invention provides a method for the chemical synthesis of a glucuronide of the formula II defined above, comprising the steps:

a) conjugating a glucuronic acid compound of the formula III:

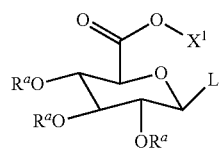

with a compound of the formula IV:

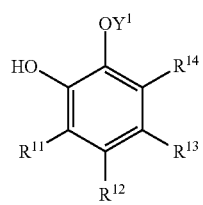

to form a conjugate of the formula V:

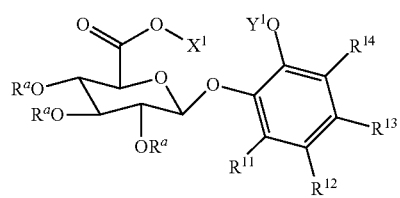

wherein L is a leaving group;

wherein $X^1$ is H, $CH_3$ or any group that can be converted to $X^2$ as in the compound of formula II to be synthesised;

wherein $Y^1$ is H or any group that can be converted to $Y^2$ as in the compound of formula II to be synthesised:

wherein each $R^a$ is a hydroxy-protecting group;

wherein $R^{11}$ is H, or any group that can be converted to $R^{21}$;

wherein $R^{12}$ is H, OH or any group that can be converted to $R^{22}$;

wherein $R^{13}$ is H, OH or any group that can be converted to $R^{23}$ provided that $R^{12}$ and $R^{13}$ are not both OH;

or $R^{12}$ and $R^{13}$ together represent a group of formula VIII:

$$—CR^{35}\!\!=\!\!CR^{36}\!\!—\!\!CR^{37}\!\!=\!\!CR^{38}\!\!— \qquad \text{VIII;}$$

wherein $R^{35}$-$R^{38}$ represent the same groups as $R^{25}$-$R^{28}$ respectively, or groups that can be converted into the respective group;

wherein $R^{14}$ is H, $NO_2$ or any group that can be converted to $R^{24}$;

b) deprotecting the groups $OR^a$ to form OH; and optionally c) converting groups $X^1$, $Y^1$, $R^{11}$, $R^{12}$, $R^{13}$, $R^{14}$, $R^{35}$, $R^{36}$, $R^{37}$ and $R^{38}$, to $X^2$, $Y^2$, $R^{21}$, $R^{22}$, $R^{23}$, $R^{24}$, $R^{25}$, $R^{26}$, $R^{27}$ and $R^{28}$; respectively.

DETAILED DESCRIPTION OF THE INVENTION

The method of detecting the β-D-glucuronidase activity E. coli in a microbial growth medium is used extensively in the analysis of drinking water. Authorities mandate strict tolerances for this indicator organism in drinking water, therefore assays must be capable of detecting even a single E. coli in a sample. Detection at such low tolerances can only be achieved by multiplying the bacterium in the first instance, essentially increasing the signal intensity of any subsequent assay. Thus, the method provides a liquid growth medium, suitable for the growth of E. coli and other β-D-glucuronidase-producing coliforms (e.g., Shigella and Salmonella), which includes a β-D-glucuronide substrate, comprising a glycosidic bond, cleavable by β-D-glucuronidase, and a metal compound that reacts with the cleaved aromatic diol moiety once the glycosidic bond is cleaved.

The liquid medium in the fourth aspect of the invention is preferably a liquid growth medium, i.e. any medium that is suitable for microbial growth. In this specification reference to liquid means liquid according to the conventional sense of the word, and would be understood by the skilled person to mean free flowing or capable of being poured. In this context liquid media can also refer to viscous liquids, viscosified to provide easier handling and resistance to spillage from the incubation vessel in such an assay. Such viscosity can result from, for example, the addition of agar or other gelling agents in amounts too low to form conventional plate media. Concentrations of agar less than 0.5% should be effective in the present invention.

The above method is distinguished from plate assays in that it is unnecessary to pinpoint individual colonies, and therefore the medium is not required to be so solid as to maintain colonies in a single orientation. Solid media, such as agar gel plate media, are able to maintain pinpoint colonies and may be incubated upside down because the concentration of agar is sufficient to create and maintain a firm gel. In contrast, media of the present invention are always sufficiently liquid to flow under any incubation conditions. In the invention microbes may diffuse through the medium. The substrate and the cleavage product may diffuse through the medium also. They and the complex of the cleavage product with the metal ion or the metal compound may be fully or partially soluble in the medium.

The microbes for which the present invention is particularly suited, generally comprise bacteria to be detected. Microbial and bacterial growth media are composed of various nutrients to support the growth of the microbial cultures. Such nutrients may include a carbon source, nitrogen source, a source of usable potassium, amino acids, salts, vitamins and cofactors, metabolic intermediates and minerals.

Carbon sources may include tryptone, peptone, casein and sugars, preferably lactose and glucose.

Nitrogen sources may include amino acids, tryptone, peptone, casein extract, and ammonium sulphate.

Salts may include ferric chloride, copper sulfate, manganese sulfate, potassium chloride, potassium iodide, zinc sulfate, magnesium chloride, potassium phosphate monobasic, potassium phosphate dibasic, sodium carbonate, magnesium sulfate, sodium chloride, calcium chloride and sodium pyruvate.

Vitamins may include biotin, pantothenate, folic acid, inositol, p-aminobenzoic acid, pyridoxine hydrochloride, riboflavin and thiamine.

A common source of amino acids, vitamins and minerals, as well as carbon and nitrogen is yeast extract, which may form part of the growth medium. Blood may also be used to supplement growth media with necessary nutrients.

Additionally, a microbial growth medium may contain antibacterial or antifungal compounds to aid in selecting and amplifying the microbes of interest.

Detergents may be included to act as dispersing agents, without any antibacterial activity.

The β-D-glucuronide substrate is a glucuronide derivative of a vicinal aromatic diol. The free diol moiety is capable of chelating the metal of the metal compound, which is preferably an iron compound. The metal-diol complex is coloured and thus suitable to report the presence of β-D-glucuronidase activity. Prior to cleavage by a β-D-glucuronidase, one of the hydroxyl oxygen atoms is bound to the glucuronide moiety via a glycosidic bond, which prevents chelation and hence colour formation. Thus, it is only in the presence of a β-D-glucuronidase, which cleaves the glycosidic bond that a colour develops in the method of claim 1.

In the β-D-glucuronidase substrate the preferred variable groups are explained below with reference to general formula I. The same preferences apply to the corresponding groups in the compound of formula II.

X can be selected from the group consisting of H, $C_{1-6}$ alkyl, $NH_4^+$, cyclohexylammonium, primary ammonium, secondary ammonium, tertiary ammonium, quaternary ammonium, 2-methyl-1,3-propanediol-2-ammonium, phenylammonium, 4-methylphenylammonium, 2-methylphenylammonium, lithium, sodium, potassium, caesium, calcium, magnesium, rubidium, strontium or barium;

Y is independently selected from the group consisting of H, a metal cation and a non-metal cation.

The line or bond drawn between X and O, and between Y and O, can represent a covalent or ionic bond. X and Y may preferably together represent the same divalent cation, which is simultaneously coordinated to both of the oxygen atoms depicted as being bonded to X and Y. When X and Y are metal cations, they can both be the same.

In an embodiment $R^1$ is H or OH and $R^4$ is H; in another embodiment, $R^1$ and $R^4$ are independently selected from the group consisting of H, $C_1$-$C_8$ alkyl, alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_1$-$C_{24}$ aryl, sulfonyl and amido. In a preferred embodiment $R^1$ and $R^4$ are both H. Acyl and acyloxy are usually lower alkanoyl and lower alkanoyloxy, respectively, such as $C_2$-$C_6$ alkanoyloxy.

In an embodiment $R^2$ and $R^3$ are independently selected from the group consisting of H, OH, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido, provided that $R^2$ and $R^3$ are not both OH. In another embodiment, $R^2$ and $R^3$ together with the atoms to which they are attached form a fused phenyl ring. Thus $R^2$ and $R^3$ together represent the formula VI: —$CR^5$=$CR^6$—$CR^7$=$CR^8$— VI; wherein $R^5$-$R^8$ are independently selected from the group consisting of H, OH, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido provided that any vicinal groups $R^5$ to $R^8$ are not both OH. Acyl and acyloxy groups $R^2$ and $R^3$ and $R^5$ to $R^8$ usually are alkanoyl and alkanoyloxy, respectively preferably lower alkanoyl and lower alkanoyloxy, respectively but may alternatively be benzoyl and benzoyloxy, respectively.

Where $R^2$ and $R^3$ represent separate groups preferably one of them is H. Where $R^2$ and $R^3$ are used to form said formula VI, preferably at least two of the groups $R^5$-$R^8$ are H, and often three, sometimes all of the groups are H. Although one or more of $R^5$-$R^8$ may be OH, any vicinal groups must not both be OH.

In an embodiment $R^2$ is OH and $R^3$ is H. In another embodiment $R^3$ is OH and $R^2$ is H. In another embodiment $R^2$ and $R^3$ are joined to form said formula VI and $R^5$-$R^8$ all represent H. The corresponding compounds of formula II, i.e. where $R^{22}$, $R^{23}$ and $R^{25}$-$R^{28}$ represent the groups indicated for $R^2$, $R^3$, $R^5$-$R^8$ respectively, are embodiments.

In an embodiment of the substrate of formula I, $R^4$ is H. In an alternative embodiment of the substrate $R^4$ is $NO_2$.

In both these embodiments $R^2$ and $R^3$ may be linked to form said formula VI.

In an embodiment of the preferred substrate of formula II, $R^{24}$ is H. In an alternative embodiment $R^{24}$ is nitro ($NO_2$). In both these embodiments $R^{22}$ and $R^{23}$ may be said linked group VII.

Preferably, the β-D-glucuronidase substrate s 1,2-dihydroxybenzene-β-D-glucuronide (catechol-β-D-glucuronide), 1,2,3-trihydroxybenzene-β-D-glucuronide (pyrogallol-2-β-D-glucuronide) or 2,3-dihydroxynaphthalene-β-D-glucuronide (DHN-β-D-glucuronide), or 1-nitro-2,3-dihydroxynaphthalene-β-D-glucuronide.

To generate a colour, the cleaved diol must chelate an ion, which is derived from a metal compound. The metal compound is preferably an iron compound and most preferably a water soluble iron salt of an organic or inorganic acid, e.g. iron (III) ammonium citrate, iron(II) gluconate, iron(II) acetate, iron(II) citrate, and iron(II) chloride. The iron compound can be iron(I) or iron(III). It will be appreciated by the skilled person that at least trace quantities of iron may be present in media or samples; however, it is necessary to supplement the medium with sufficient quantities of an iron compound for the invention to work. The concentration of iron in the growth medium is preferably 0.2 to 1 g/l.

It may be desirable to use the method in conjunction with a substrate capable of detecting β-D-galactosidase activity, preferably o-nitrophenyl-β-D-galactopyranoside (ONPG). Many coliforms other than E. coli produce β-D-galactosidase, however in the context of drinking water testing, it is E. coli that is most important to detect. It is therefore important that the colour resulting from the β-D-galactosidase test does not interfere with or mask the colour produced by the β-D-glucuronide substrate in the presence of an iron compound and a β-D-glucuronidase. It was found that the pale yellow colour of the ONPG substrate does not interfere with visualising the darker colour of the β-D-glucuronide substrate upon cleavage, thereby leaving the method sensitive to E. coli, the indicator organism of greatest interest. The method of the first aspect of the invention is useful for detecting the presence of microbes, for instance microbial contamination of food, drinks, or water that will come into contact with humans or animals. The method may be carried out according to routine test protocols and using standard sampling methods and growth stages. The results are observed visually or by machine, usually with incident visible light. Incubation may be overnight, but for samples with high levels of enzyme already present shorter incubation may be sufficient, for instance after 1 hour's incubation, sometimes 4-6 hours incubation. Incubation temperatures are selected according to the species being detected and may be at room temperature, but is more often at raised temperature in the range of 30 to 50° C., preferably in the range 35 to 45° C.

The liquid medium composition of the fourth aspect may comprise agar or any other gelling agent in order to increase the viscosity of the medium to provide ease of handling.

The liquid medium composition may also comprise one or more inducers of β-D-glucuronidase, such as glucuronate and/or a β-D-glucuronide which differs from the chromogenic β-D-glucuronidase substrate of the present invention.

The fifth aspect of the invention provides the composition of the fourth aspect as a concentrate. In this context, a concentrate can be dry, e.g. a mixture of dry components, such as a powder, or a concentrate can be a liquid or solution that is more concentrated than the final working concentration of the liquid media composition. Such concentrates are suitable for dilution with water, and preferably, in the case of an assay of water quality, directly by dilution with the water to be sampled.

The sixth aspect of the invention provides a method of chemical synthesis as described above. The conjugation step of the synthesis may be acid or base catalysed. Acid catalysis may be carried out using the usual synthetic techniques and acids such as p-toluenesulfonic acid or another Lewis acid. Base catalysis may use conventional techniques such as an alkali metal hydroxide. The deprotection step may be carried out with an alkali, an acid or by hydrogenolysis. The synthesis involves the protected glucuronic acid compound of formula III. Protecting groups $R^a$ are selected from protecting groups conventionally used in sugar conjugation, for instance acetyl, benzoyl or benzyl. They are all the same, so that they may subsequently be deprotected in the same step.

Preferably $X^1$ is $CH_3$.

Preferably $Y^1$ is the same as $Y^2$.

The leaving group L is selected from conventional leaving groups. Examples are halogen, preferably Br, and acyloxy, preferably acetoxy or trichloroacetimidyloxy.

For convenience, the groups, $Y^1$, $R^{11}$, $R^{12}$, $R^{13}$ and $R^{14}$ are the same as $Y^2$. $R^{21}$, $R^{22}$, $R^{23}$ and $R^{24}$ respectively. Where they are groups that need to be converted, the method includes the step of carrying out that conversion. For instance a group $R^{11}$, $R^{12}$ or $R^{13}$ may be protected phenolic OH and converted into OH in the compound of formula II by a deprotection step.

$X^1$ may be the same as $X^2$. In another embodiment $X^1$ is not the same as $X^2$.

Similarly where $X^1$ or $Y^1$ need converting to $X^2$ or $Y^2$, respectively, the method involves the conversion step, e.g. a hydrolysis, or a salt forming step; for instance $X^1$ as $CH_3$ may be converted by hydrolysis to leave the free acid ($X^2$ is H) or a salt ($X^2$ is a metal or non-metal cation). Preferably $Y^1$ is the same as $Y^2$ so that no conversion is necessary.

The β-D-glucuronidase substrates of the present invention, particularly used in a method of detecting bacteria as detailed above, are an improvement over the technical problems (mentioned above) associated with known β-D-glucuronidase substrates. They are highly water soluble and chromogenic, thus, they are well suited to liquid-phase assays and do not require any special equipment to detect a signal.

The invention will now be described by way of example, which should in no way imply that the invention is limited by the following examples.

EXAMPLES

Examples 1 to 7 relate to the synthesis of the β-D-glucuronides. Reagents and solvents were purchased from Sigma-Aldrich (Gillingham, UK), Alfa Aesar (Heysham, UK) or Univar (Widnes. UK) except where stated differently. Flash column chromatography was performed on silica gel C60 (Fluorochem, Derbyshire, UK). Thin layer chromatography (TLC) was carried out using pre-coated silica plates (0.2 mm, UV 254). These were developed using UV fluorescence at 254 nm and 366 nm followed by spraying with $H_2SO_4$/MeOH and heating. Mixed solvent compositions are reported as volumetric ratios. NMR spectra were recorded on a 270 MHz Joel NMR spectrometer (at 270 MHz for 1H and 68 MHz for 13C) or NMR spectra were recorded on a 400 MHz Joel NMR spectrometer (at 400 MHz for 1H and 100 MHz for 13C). All chemical shifts are quoted in ppm relative to TMS. Optical rotations were measured on an Optical Activity AA10 polarimeter. Melting points were determined with an Electrothermal AI9200 apparatus and are uncorrected. All melting points are quoted to the nearest 0.5° C. High Resolution Mass Spectroscopy (HRMS) data were obtained using the EPSRC mass spectrometry service centre (Swansea, UK).

Example 1

Catechol β-D-Glucuronide CHA Salt (Compound 1)

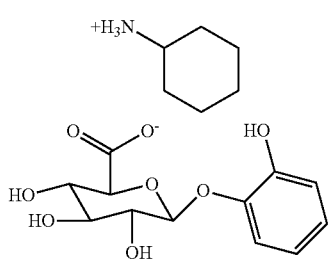

Compound 1

Compound 3 (5.46 g see Example 4 below) was dissolved in acetone (75 mL). A solution of NaOH (2.81 g) in deionised (DI) water (37.5 mL) was added. The reaction mixture formed 2 layers which were stirred at room temperature for 2 hours. TLC showed complete deprotection. The solution was passed down a column of Amberlite® IR 120 H+ ion exchange resin (50 g). Fractions containing the product were combined and basified using cyclohexylamine (CHA) (5 mL). The solution was left at +4° C. overnight then concentrated under reduced pressure to give an amber oil. The oil was triturated in industrial methylated spirits (IMS) (100 mL). A white precipitate formed and the mixture was left at +4° C. overnight. The white precipitate was recovered by filtration to give compound 1 as a white solid (3.23 g, 65%). m.p. 208-210° C. $[\alpha]_D^{22}$ −51° (c 0.504 in water). $^1$H-NMR: (DMSO-d$_6$) δ 7.09, (1H, dd, J 1.48 Hz, J 7.92 Hz), 7.83 (2H, q, d, J 1.48 Hz, J 7.92 Hz, J 1.98 Hz), 6.72 (1H, m, J 1.98 Hz), 4.65 (1H, d, J 7.42 Hz), 3.45 (1H, d, J 9.40 Hz, H), 3.28-3.16 (2H, m), 2.89 (1H, m), 1.86-1.53 (5H, m), 1.25-1.03 (5H, m). $^{13}$C NMR: (CDCl$_3$) δ172.99, 147.86, 146.06, 123.73, 119.79, 118.25, 116.72, 103.23, 76.35, 74.49, 73.61, 72.71, 49.65, 31.13, 25.15, 24.34.

Example 2

DHN-β-D-Glucuronide Sodium Salt (Compound 2a)

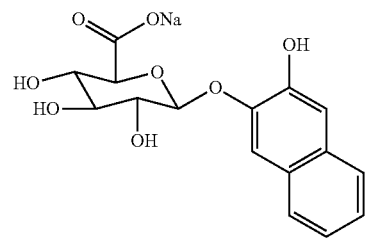

Compound 2a

Compound 5 (1.56 g see Example 6 below) was dissolved in acetone (21 mL). A solution of NaOH (0.446 g) in DI water (1 mL) was added. The mixture was stirred at room temperature overnight. TLC showed no remaining protected material. A brown precipitate had formed in the solution. This solid was collected by filtration to give the desired compound 2a (1.16 g. 99%). m.p. 53-55° C., $[\alpha]_D^{23}$ −25° (c 0.995 in water). $^1$H-NMR (DMSO-d$_6$): δ 7.62 (2H, m), 7.45 (1H, s), 7.25 (2H, m, J 6.93 Hz), 7.17 (1H, s), 4.91 (1H, d, J 6.90 Hz), 3.53 (1H, d, J 9.60 Hz), 3.26 (3H, m).

Example 3

DHN-β-D-Glucuronide CHA Salt (Compound 2b)

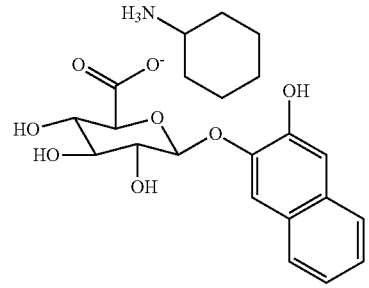

Compound 2b

Compound 5 (6.1 g) was dissolved in acetone (75 mL). A solution of NaOH (2.81 g) in DI water (37.5 mL) was added. The mixture was stirred at room temperature for 2 hours. TLC showed no remaining protected material. The solution was passed down an Amberlite® IR120 H$^+$ ion exchange resin column (50 g). The eluent containing the product was basified using CHA (5 mL). A white precipitate formed. The mixture was left at +4° C. overnight. The white fluffy solid was collected by filtration, washing with DI water then acetone to give compound 2b as a white, fluffy solid (2.8 g, 53%). m.p. 223-224° C., $[\alpha]_D^{19}$ –96° (c 0.5 in water). $^1$H-NMR (DMSO-d$_6$): δ 7.64 (2H, m), 7.46 (1H, s), 7.28 (21H, m, J 6.93 Hz), 7.20 (1H, s), 4.95 (1H, d, J 6.93 Hz), 3.58 (1H, d, J 9.40 Hz), 3.35 (2H, m, J 6.68 Hz. J 9.65 Hz. J 8.16 Hz), 3.24 (1H, m), 1.92-1.48 (5H, m), 1.23-1.05 (5H, m); $^{13}$C NMR (DMSO-d$_6$): δ 172.73, 147.80, 147.13, 130.74, 128.73, 127.25, 126.32, 124.87, 123.72, 112.14, 110.68, 99.98, 76.64, 74.81, 73.64, 72.81, 49.63, 30.99, 25.09, 24.27. HRMS (ESI) for C$_{16}$H$_{16}$O$_8$ [M+H]$^+$: m/z calcd 335.0772. measured: 335.0767.

Example 4

Catechol 2',3',4',-tri-O-acetyl β-D-glucuronide-6'-methyl ester (Compound 3)

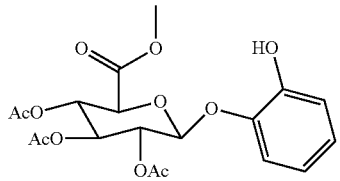

Compound 3

1,2,3,4-Tetra-O-acetyl-β-D-glucuronide-6-methyl ester (MTAG) [G. N. Bollenback et al, J. Am. Chem. Soc., 77, 3310, (1955)](Glycosynth Ltd) (20 g), catechol (11.8 g) and p-toluenesulfonic acid (PTSA) (514 mg) were stirred under reduced pressure on a rotary evaporator for 50 minutes at 70-75° C. The brown oil was dissolved in dichloromethane (DCM) (100 mL) and washed with 1M NaOH (3×50 mL) and DI water (2×50 mL) before being dried (MgSO$_4$) and concentrated under reduced pressure to give a pale yellow solid. The obtained yellow solid was triturated in IMS (20 mL) and the so obtained solid was recovered by filtration and slurried in MeOH (20 mL). The undissolved white solid was collected by filtration. TLC showed the obtained solid was a mixture of unreacted MTAG and catechol. The filtrate was concentrated under reduced pressure to produce a pink solid which was triturated in IMS (20 mL). The resultant white solid was collected by filtration to give compound 3 (2.5 g, 11%). m.p. 128-130° C. [lit., Bollenback et al, loc. cit. 136-137° C.]. $[\alpha]_D^{20.5}$ –27° (c 0.37 in acetone) [lit., Bollenback at al, loc. cit. $[\alpha]_D$ –33.4° (c 1 in CHCl$_3$)].

Example 5

Catechol β-D-Glucuronide-6'-Methyl Ester Compound 4

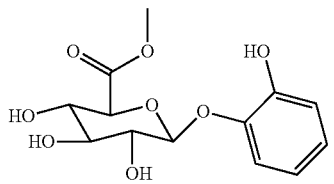

Compound 4

Compound 3 (1.5 g) was dissolved in acetone (10 mL) and DI water (6.3 mL). A solution of NaOH (785 mg) in DI water (4 mL) was added and the orange solution left at room temperature for 4 hours. TLC showed no remaining fully protected material. The solution was acidified to pH 1 using conc. HCl. The solution was concentrated under reduced pressure to produce a brown oil. The brown oil was triturated in MeOH (10 mL) and left at +4° C. overnight. Sodium chloride precipitated overnight, and this was removed by filtration and washed with MeOH (0.5 mL). The combined filtrate was concentrated under reduced pressure to a brown foam. The brown foam was purified by flash chromatography using C$_{60}$ silica gel (40 g) eluting with DCM/MeOH 10:1 v/v, collecting fractions of approx. 100 mL. Fractions 17-24 were combined and concentrated under reduced pressure to give compound 4 (485 mg, 48%) as a pale amber foam. $[\alpha]_D^{21}$ –80° (c 0.688 in water). $^1$H-NMR: (DMSO-ds) δ 8.62 (1H, s). 6.95 (1H, dd, J 1.14 Hz, J 8.01 Hz), 6.80 (2H, m, J 1.37 Hz, J 9.62 Hz), 6.69 (1H, m, J 1.37 Hz, J 7.78 Hz), 5.57 (1H, s), 5.42 (1H, s), 5.26 (1H, s), 4.88 (1H, d. J 7.3 Hz), 4.00 (1H, d, J 9.60 Hz), 3.37 (1H, m, J 9.16 Hz), 3.32 (1H, s), 3.30 (2H, broad m); $^{13}$C NMR: (CDCl$_3$) δ169.90, 147.40, 145.30, 123.63, 119.81, 116.97, 116.69, 102.06, 75.70, 75.46, 73.55, 71.99, 52.21.

Example 6

DHN-2',3',4'-tri-O-acetyl-β-D-glucuronide-6-methyl ester (Compound 5)

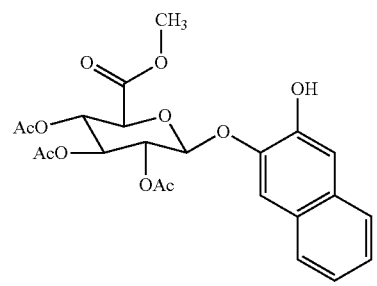

Compound 5

A mixture of 2,3-dihydroxynaphthalene (D N) (34.4 g) and MTAG (40 g) was heated in an oil bath to 120° C. on a rotary evaporator under reduced pressure until a homogeneous melt was obtained. PTSA (150 mg) in 1:1 v/v acetic acid/acetic anhydride (AcOH/Ac$_2$O) (1 mL) was added and the mixture stirred at 120° C. on a rotary evaporator under reduced pressure for 1 hour. TLC showed some remaining MTAG, therefore PTSA (150 mg) in 1:1 v/v AcOH/Ac$_2$O (1 mL) was added and the mixture stirred at 120° C. under reduced pressure for a further 30 min. TLC then showed no remaining MTAG. The dark oil was allowed to cool to room temperature overnight before being dissolved in DCM (300 mL). The solution was washed with sat. NaHCO$_3$ (4×50 mL), DI water (500 mL) and brine (500 mL) before being dried (MgSO$_4$) and concentrated under reduced pressure to give a brown foaming oil (59.1 g). The foam was purified by flash chromatography using C$_{60}$ silica gel (1 Kg), eluting with toluene/acetone 10:1 v/v, collecting fractions of 200 mL. Fractions 19-26 were combined and concentrated under reduced pressure to produce a red solid (29.66 g). The red solid was triturated in IMS (150 mL) and left at +4° C. overnight to complete crystallisation. The resultant pale yellow fluffy solid was collected by filtration to give compound 5 (12.6 g, 25%). m.p. 191-192° C., $[\alpha]_D -26°$ (c 0.5 in CHCl$_3$). $^1$H-NMR (DMSO-d$_6$): δ 9.80 (1H,), 9.67 (2H, dd, J 7.97 Hz, J 12.62 Hz), 7.45 (1H, s), 7.28 (2H, m), 7.18 (1H, s), 5.69 (1H, d, J 7.67 Hz), 5.48 (1H, t, J 9.65 Hz), 5.13 (2H, m, J 9.65 Hz, J 7.92 Hz), 4.71 (1H, d, J 9.90 Hz), 3.63 (3H, s), 2.01, 2.00, 1.99 (4×3H, 4×s); $^{13}$C NMR (DMSO-d$_6$): δ 170.12, 169.92, 169.59, 167.80, 148.17, 146.35, 131.22, 128.19, 127.33, 126.16, 123.89, 114.05, 110.96, 98.74, 71.75, 71.63, 71.31, 69.58, 53.15, 21.03, 20.91, 20.81. HRMS (ESI) for CH$_{23}$H$_{28}$O$_{11}$N [M+NH$_4$]$^+$: m/z calcd 494.1657. measured: 494.1646.

Example 7

DHN-β-D-Glucuronide-6'-Methyl Ester (Compound 6)

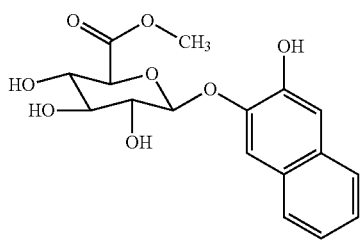

Compound 6

Compound 5 (1.0 g) was suspended in methanol (3 mL) and NaOMe solution in methanol (2.17 M, 0.6 mL) was added. The solid slowly dissolved and a cream precipitate began to form. The mixture was neutralised to ~pH 6-7 using AcOH (0.2 mL). The solid dissolved giving an orange solution which was concentrated under reduced pressure to give compound 6 as an orange foam (849 mg) which appeared to contain about 15% inorganic salt. $[\alpha]_D^{19} -100°$ (c 0.1 in water). $^1$H-NMR (DMSO-d$_6$): δ 7.64 (2H, m), 7.40 (1H, s), 7.25 (2H, m), 7.16 (1H, s), 5.15 (1H, d, J 6.93 Hz), 4.13 (1H, d, J 9.15 Hz), 3.69 (3H, s) 3.42 (3H, m, J 6.93 Hz, J 9.15 Hz, J 8.16 Hz); $^{13}$C NMR (DMSO-d$_6$): δ 169.95, 148.36, 147.03, 130.88, 128.28, 127.16, 126.12, 124.88, 123.52, 111.64, 110.87, 101.58, 81.97, 75.91, 75.68, 73.52, 72.13, 52.51. HRMS (ESI) for C$_{17}$H$_{22}$O$_8$N [M+NH$_4$]$^+$: m/z calcd 368.1340. measured; 368.1339.

Example 8

The specificity of action of both DHN-β-D-glucuronide (2) and of catechol-β-D-glucuronide (1), as well as their 6'-methyl esters (4 and 6), was first established using multi-point inoculation of 20 different microbial strains onto Columbia agar plates. The strains chosen represented species commonly encountered in diagnostic microbiology. The substrates were incorporated into the agar at a concentration of 300 mg/L with an iron salt, ferric ammonium citrate, (hereinafter known as FAC) at 500 mg/L. The plates were incubated for 18 h at 37° C. in air. The results are shown in Table 1 below.

TABLE 1

| Organism | Catechol-β-D-glucuronide 1 Colour | Catechol-β-D-glucuronide-6'-methyl ester 4 Colour | DHN-β-D-glucuronide sodium salt 2a Colour | DHN-β-D-glucuronide CHA salt 2b Colour | DHN-β-D-glucuronide-6'-methyl ester 6 Colour |
|---|---|---|---|---|---|
| 1 *Escherichia coli* NCTC 10418 | ++ | + | ++ | ++ | + |
| 2 *Klebsiella pneumoniae* NCTC 9528 | − | − | − | − | − |
| 3 *Providencia rettgeri* NCTC 7475 | − | − | − | − | − |
| 4 *Enterobacter cloacae* NCTC 11936 | − | − | − | − | − |
| 5 *Serratia marcescens* NCTC 10211 | − | − | − | − | − |
| 6 *Salmonella typhimurium* NCTC 74 | − | − | − | − | − |
| 7 *Pseudomonas aeruginosa* NCTC 10662 | − | − | − | − | − |
| 8 *Yersinia enterocolitica* NCTC 11176 | − | − | − | − | − |
| 9 *Burkholderia cepacia* NCTC 10931 | − | − | − | − | − |
| 10 *Acinetobacter baumanaii* NCTC 19606 | − | − | − | − | − |
| 11 *Streptococcus pyogenes* NCTC 8306 | − | − | − | − | − |
| 12 *Staphylococcus aureus* (MRSA) NCTC 11939 | − | − | − | − | − |
| 13 *Staphylococcus aureus* NCTC 6571 | − | − | − | − | − |
| 14 *Staphylococcus epidermidis* NCTC 11047 | − | − | − | − | − |
| 15 *Listeria monocytogenes* NCTC 11994 | − | − | − | − | − |
| 16 *Enterococcus faecium* NCTC 7171 | − | − | − | − | − |
| 17 *Enterococcus faecalis* NCTC 775 | − | − | − | − | − |
| 18 *Bacillus subtilis* NCTC 9372 | − | − | − | − | − |
| 19 *Candida albicans* ATCC 90028 | − | − | − | − | − |
| 20 *Candida glabrata* NCPF 3943 | − | − | − | − | − |

++ means strong colour;

+ means less colour than ++;

− means no colour

Of the 20 strains, only the β-D-glucuronidase-positive strain of *E. coli*, (*E. coli* NCTC 10418) was able to hydrolyse the substrates. This organism generated diffuse, purple-brown colonies with the catechol substrates and diffuse, maroon colonies with the DHN substrates. Essentially identical results were obtained if other iron salts (e.g. iron(II) gluconate, iron(II) acetate, iron(II) citrate, iron(II) acetylacetonate and iron(III) acetylacetonate) were substituted in place of FAC. The iron compound can be either iron(II) (i.e. ferrous) or iron(III) (i.e. ferric). Both types of compound work equally, and the coloured chelates were still formed when the plates were incubated under anaerobic conditions, which is another useful feature of the present invention. The substrates may also be autoclaved at 116° C. for 20 minutes with no decrease in sensitivity. It will be appreciated that the media and the reagents will all contain at least traces of iron compounds. However, the invention does not work unless the medium is supplemented with a sufficient amount of an iron compound. Concentrations of 200-600 mg/L of iron compound were found to be satisfactory. In contrast, supplementing the growth media with compounds of other metals gave either no coloured endpoint or an extremely poor one to visualise. The other 19 organisms tested uniformly negative with all five substrates (1, 2a, 2b, 4 and 6), showing the complete specificity of each substrate for *E. coli*. None of the substrates affected the growth of any organism to any apparent extent, but the intensity of the colour given by the two 6'-methyl esters (4 and 6) was noticeably inferior to that produced by the fully deprotected glucuronides. Therefore the latter substrates were preferred for more extensive evaluation. DHN-β-D-glucuronide sodium salt (2a) performed the same as its CHA salt (2b). For convenience, further evaluation of catechol-β-D-glucuronide and DHN-β-D-glucuronide was conducted with the CHA salt forms only (1 and 2b). In the present invention the counter ion of the glucuronide is not considered to be of special significance. For acidic enzyme substrates (including glucuronides), a variety of different counter ions, both inorganic and organic, are well known in the prior art.

Example 9

In order to obtain a fuller picture of the sensitivity of the substrates, they were screened with 100 different clinical isolates of *E. coli* in a liquid medium containing FAC. The isolates were chosen at random from the Microbiology Department, Freeman Hospital, Newcastle Upon Tyne, UK. The effectiveness of the new substrates was compared with three other media which all contained indoxyl-β-D-glucuronides. One was a commercial medium, CPS ID 3 (bioMérieux SA, Lyon, France). CPS ID 3 contains complementary chromogenic substrates; Rose-β-D-glucuronide (6-chloro-3-indolyl β-D-glucuronide) of undisclosed salt form [at 250 mg/L] for the detection of β-D-glucuronidase activity (producing red or pink colonies) and X-β-D-glucoside (5-bromo-4-chloro-3-indolyl β-D-glucopyranoside) [50 mg/L] for the detection of β-D-glucosidase (producing green colonies) [M. Casse et al, U.S. Pat. No. 8,216,802 (2012)]. This medium was employed as a control. Among the β-D-glucuronidase producing strains of *E. coli* there is a large variation in the quantity of the enzyme produced and it is almost certain that the CPS ID 3 medium has been rigorously optimised to allow good growth of all the target organisms and maximum expression of the target enzymes. Therefore, two indoxyl glucuronides, X-β-D-glucuronide CHA salt and Rose-β-D-glucuronide CHA salt were also tested in a simple agar medium to allow a direct comparison of the sensitivity of these Indoxyl glucuronides when used in a medium that has not been optimised for the growth of the target organism. The comparison of the results for Rose-β-D-glucuronide and the CPS ID 3 medium was of particular significance as the commercial medium also uses Rose-β-D-glucuronide for the detection of *E. coli*. For consistency, the four glucuronides were all chosen as their CHA salts. As already stated, it is not anticipated that the salt form is critical to their performance. Currently. X-β-D-glucuronide is often used as either the CHA salt or the sodium salt. Brenner and colleagues [K. P. Brenner et al, Appl. Environ. Microbiol., 59, 3534-3544, (1993)] found no difference in the performance of the CHA and sodium salt forms with their application using indoxyl-β-D-glucuronide, neither in respect of colour development nor in the recovery of *E. coli*.

The two indoxyl glucuronides used produce insoluble endpoints following hydrolysis, as does the CPS ID 3 medium. It was therefore necessary to test these two substrates on agar plates. In contrast, catechol-β-D-glucuronide (1) and DHN-β-D-glucuronide (2b) give much more soluble endpoints best suited to liquid media and were therefore tested in a broth medium. Each broth was prepared using proteose peptone (Oxoid, Basingstoke, UK) (2 g), NaCl (1 g) and FAC (100 mg) in DI water (180 mL). This mixture was autoclaved and cooled to room temperature before being dispensed into bijoux (100×1.8 mL). Catechol β-D-glucuronide CHA salt (1) or DHN-β-D-glucuronide CHA salt (2b) (60 mg) were each dissolved in water (20 mL) and filtered to sterilize before being aseptically dispensed into successive bijoux (0.2 mL) containing the broth solution. The broth/substrate solutions were then inoculated with bacterial suspensions made up to 0.5 McFarland standard (2 μL per bijoux). X-β-D-glucuronide CHA salt (Glycosynth Ltd, Warrington, UK) (10 mg) was dissolved in NMP (200 μL). Rose-β-D-glucuronide CHA salt (Glycosynth Ltd, Warrington, UK) (20 mg) was dissolved in NMP (200 μL). These solutions were then added to Columbia agar (Oxoid, Basingstoke, UK) (100 mL) and inoculated with bacterial suspensions made up to 0.5 McFarland standard (1 μL). The strains of *E. coli* used are listed in table 2. The plates and broths were incubated at 37° C. for 18 hours in air. The green colonies seen on the CPS ID 3 media were indicative of β-D-glucosidase activity.

TABLE 2

| Ref | Organism | Reference | CPS ID 3 agar | X-β-D-glucuronide CHA salt | Rose-β-D-glucuronide CHA salt | Catechol-β-D-glucuronide CHA salt 1 broth | DHN-β-D-glucuronide CHA salt 2b broth |
|---|---|---|---|---|---|---|---|
| 1 | *E. coli* | 260471B | +/−Red | — | — | — | — |
| 2 | *E. coli* | 260464G | Red | Green | Red | Black | Purple |
| 3 | *E. coli* | 260481J | Red | Green | Red | Black | Purple |
| 4 | *E. coli* | 260480M | Red | Green | Red | Black | Purple |
| 5 | *E. coli* | 260521S | Red | Green | Red | Black | Purple |
| 6 | *E. coli* | 260578D | +/−Red | — | — | — | — |

TABLE 2-continued

| Ref | Organism | Reference | CPS ID 3 agar | X-β-D-glucuronide CHA salt | Rose-β-D-glucuronide CHA salt | Catechol-β-D-glucuronide CHA salt 1 broth | DHN-β-D-glucuronide CHA salt 2b broth |
|---|---|---|---|---|---|---|---|
| 7 | E. coli | 260537E | Red | — | — | — | — |
| 8 | E. coli | 260522Z | Red | Green | Red | Black | Purple |
| 9 | E. coli | 260541R | +/−Red | Green | Red | Black | Purple |
| 10 | E. coli | 260538H | Red | — | — | — | — |
| 11 | E. coli | 260539Y | Red | Green | Red | Black | Purple |
| 12 | E. coli | 260545G | Red | Green | Red | Black | Purple |
| 13 | E. coli | 260459W | Red | Green | Red | Black | Purple |
| 14 | E. coli | 260458Y | Red | Green | Red | Black | Purple |
| 15 | E. coli | 260441G | Red | Green | Red | Black | Purple |
| 16 | E. coli | 260440S | Red | Green | Red | Black | Purple |
| 17 | E. coli | 260508Y | Red | Green | Red | Black | Purple |
| 18 | E. coli | 260504N | Red | Green | Red | Black | Purple |
| 19 | E. coli | 260503Z | Red | Green | Red | Black | Purple |
| 20 | E. coli | 260554D | Red | Green | Red | Black | Purple |
| 21 | E. coli | 260502G | Red | Green | Red | Black | Purple |
| 22 | E. coli | 260532S | Red | Green | Red | Black | Purple |
| 23 | E. coli | 260533G | Red | Green | Red | Black | Purple |
| 24 | E. coli | 260536Q | Red | Green | Red | Black | Purple |
| 25 | E. coli | 260548Q | Red | Green | Red | Black | Purple |
| 26 | E. coli | 260549E | Red | Green | Red | Black | Purple |
| 27 | E. coli | 260553X | — | — | — | — | — |
| 28 | E. coli | 260547N | Red | Green | Red | Black | Purple |
| 29 | E. coli | 260563B | Red | Green | Red | Black | Purple |
| 30 | E. coli | 260564R | Red | Green | Red | Black | Purple |
| 31 | E. coli | 260555L | Red | Green | Red | Black | Purple |
| 32 | E. coli | 260511X | Red | Green | Red | Black | Purple |
| 33 | E. coli | 260515Z | Red | — | Red | Black | Purple |
| 34 | E. coli | 260514G | Red | — | — | — | — |
| 35 | E. coli | 260505Q | Red | — | — | — | — |
| 36 | E. coli | 260510R | Red | Green | Red | Black | Purple |
| 37 | E. coli | 260364H | Tr. Red | — | — | Black | — |
| 38 | E. coli | 260406Y | Red | Green | Red | Black | Purple |
| 39 | E. coli | 260492J | Red | Green | Red | Black | Purple |
| 40 | E. coli | 260486L | Red | Green | Red | Black | Purple |
| 41 | E. coli | 260485D | Red | Green | Red | Black | Purple |
| 42 | E. coli | 260479Q | Red | Green | Red | Black | Purple |
| 42 | E. coli | 260506E | Red | Green | Red | Black | Purple |
| 44 | E. coli | 260478N | Tr. Red | — | — | — | — |
| 45 | E. coli | 260463D | Red | Green | Red | Black | Purple |
| 46 | E. coli | 260396Z | Red | Green | Red | Black | Purple |
| 47 | E. coli | 260370C | Red | Green | Red | Black | Purple |
| 48 | E. coli | 260262P | Red | Green | Red | Black | Purple |
| 49 | E. coli | 260280Z | Red | Green | Red | Black | Purple |
| 50 | E. coli | 260375E | Red | Green | Red | Black | Purple |
| 51 | E. coli | 260400N | — | — | — | — | — |
| 52 | E. coli | 260404W | Red | Green | Red | Black | Purple |
| 53 | E. coli | 260401Q | Red | Green | Red | Black | Purple |
| 54 | E. coli | 260402H | Red | Green | Red | Black | Purple |
| 55 | E. coli | 260411Z | Red | Green | Red | Black | Purple |
| 56 | E. coli | 260407F | Red | Green | Red | Black | Purple |
| 57 | E. coli | 260408C | Red | Green | Red | Black | Purple |
| 58 | E. coli | 260509W | Red | Green | Red | Black | Purple |
| 59 | E. coli | 260433H | Red | Green | Red | Black | Purple |
| 60 | E. coli | 260432E | Red | Green | Red | Black | Purple |
| 61 | E. coli | 260431N | Red | Green | Red | Black | Purple |
| 62 | E. coli | 260428T | Red | Green | Red | Black | Purple |
| 63 | E. coli | 260426F | Red | Green | Red | Black | Purple |
| 64 | E. coli | 260425A | Red | Green | Red | Black | Purple |
| 65 | E. coli | 260483R | — | — | — | — | — |
| 66 | E. coli | 260494B | Red | Green | Red | Black | Purple |
| 67 | E. coli | 260495R | — | — | — | Black | Purple |
| 68 | E. coli | 260439C | Red | Green | Red | Black | Purple |
| 69 | E. coli | 260438F | Red | Green | Red | Black | Purple |
| 70 | E. coli | 260437A | Red | — | Tr. Red | — | — |
| 71 | E. coli | 260412Q | Red | Green | Red | Black | Purple |
| 72 | E. coli | 260497D | Red | Green | Red | Black | Purple |
| 73 | E. coli | 260416W | Red | — | — | Black | Purple |
| 74 | E. coli | 260417P | Red | Green | Red | Black | Purple |
| 75 | E. coli | 260422Y | Red | Green | Red | Black | Purple |
| 76 | E. coli | 260406A | Red | — | — | — | — |
| 77 | E. coli | 260405P | Red | Green | Red | Black | Purple |
| 78 | E. coli | 2604399E | Red | Green | Red | Black | Purple |
| 79 | E. coli | 260435W | Red | Green | Red | Black | Purple |
| 80 | E. coli | 260434Y | Red | Green | Red | Black | Purple |
| 81 | E. coli | 2603121P | Tr. Red | — | — | — | — |
| 82 | E. coli | 260310H | Red | Green | Red | Black | Purple |

TABLE 2-continued

| Ref | Organism | Reference | CPS ID 3 agar | X-β-D-glucuronide CHA salt | Rose-β-D-glucuronide CHA salt | Catechol-β-D-glucuronide CHA salt 1 broth | DHN-β-D-glucuronide CHA salt 2b broth |
|---|---|---|---|---|---|---|---|
| 83 | E. coli | 260436P | Red | Green | Red | Black | Purple |
| 84 | E. coli | 260398Q | Red | Green | Red | Black | Purple |
| 85 | E. coli | 260345F | Red | Green | Red | Black | Purple |
| 86 | E. coli | 260390B | — | — | — | — | — |
| 87 | E. coli | 260414H | Red | Green | Red | Black | Purple |
| 88 | E. coli | 260415Y | Red | Green | Red | Black | Purple |
| 89 | E. coli | 260313A | Tr. Red | — | — | — | — |
| 90 | E. coli | 260316T | — | — | — | — | — |
| 91 | E. coli | 260424P | Red | Green | Red | Black | Purple |
| 92 | E. coli | 260348K | Red | Green | Red | Black | Purple |
| 97 | E. coli | 260354W | Red | Green | Red | Black | Purple |
| 98 | E. coli | 260333P | — | — | — | — | — |
| 99 | E. coli | 260330Y | Red | Green | Red | Black | Purple |
| 100 | E. coli | 260327V | Red | Green | Red | Black | Purple |
| 101 | E. cloacae | 260329R | Tr. Green | — | — | — | — |
| 102 | E. cloacae | NCTC 11936 | Tr. Green | — | — | — | — |
| 103 | E. faecium | NCTC 7171 | Green | — | — | — | — |
| 104 | E. faecalis | NCTC 775 | Green | — | — | — | — |
| 105 | E. coli | O157 non-toxigenic | — | — | — | — | — |

Red, Green, Black or Purple mean strong colour;
+/− means less colour than strong;
Tr means a trace of colour, less than +/−;
— means no colour.

The results of table 2 (lines 1-100) are summarised below (table 3) for the 100 E. coli strains after 18 h incubation;

TABLE 3

| Substrate/Medium | Negative strains | Positive strains | % Sensitivity |
|---|---|---|---|
| CPS ID 3 agar | 7 | 93 | 93 |
| Catechol-β-D-glucuronide CHA salt 1 broth | 17 | 83 | 83 |
| DHN-β-D-glucuronide CHA salt 2b broth | 18 | 82 | 82 |
| Rose-β-D-glucuronide | 19 | 81 | 81 |
| X-β-D-glucuronide | 21 | 79 | 79 |

The commercial medium, CPS ID3, was the most sensitive with 93/100 of E. coli strains giving red colonies. The excellent performance of this medium was to be expected, as it most probably contains inducers of β-D-glucuronidase activity and/or optimal conditions for the expression of this enzyme. That not all strains were detected by this medium is understandable, as a small percentage of all E. coli strains is negative for β-D-glucuronidase. Surprisingly, the next most sensitive media were the two containing the substrates of the present invention. Catechol-β-D-glucuronide (1) [greyish-black solutions, sometimes with black flakes] detected 83/100 strains and DHN-β-D-glucuronide (2b) [purple solutions] 82/100 strains. Both the novel substrates showed higher sensitivity than Rose-β-D-glucuronide [red colonies] (81/100 strains) when it was used in the simple Columbia agar medium. Considering that Rose-β-D-glucuronide is the same substrate as employed in the CPS ID3 medium, it shows how those skilled in the art can develop a medium to increase the sensitivity of the substrate when challenged with many different strains of microorganisms. X-β-D-glucuronide [green colonies] gave the lowest sensitivity (79/100 strains) in the simple agar medium, yet this substrate is currently very extensively used in commercial media to detect E. coli. More surprising still, both catechol-β-D-glucuronide (1) and DHN-β-D-glucuronide (2b) visualised one strain (E. coli 260495R) that was not detected by CPS ID3 or by the other two media containing the indoxyl glucuronides. In addition to the 100 strains of E. coli, all five media were tested with four other stains of Enterobacteriaceae known to be β-D-glucuronidase-negative, as well as one β-D-glucuronidase-negative strain of E. coli (E. coli O157 non-toxigenic) (Table 2, lines 101-105). All five of these strains were negative on all the media, thus showing 100% specificity for β-D-glucuronidase-producing E. coli over these other organisms.

Example 10

Because many E. coli produce both β-D-glucuronidase and β-D-galactosidase, catechol-β-D-glucuronide (1) and DHN-β-D-glucuronide (2b) were tested as in the broth media described above but in the presence of o-nitrophenyl-β-D-galactoside (ONPG) (at a concentration of 1.5 g/L). This was done to see if the colour produced by the iron complexes could mask the yellow of o-nitrophenol. This would be essential to successfully visualise any E. coli in a dual-chromogenic (or possibly multi-chromogenic) system. It was found that E. coli expressing both β-D-glucuronidase and β-D-galactosidase now gave purple-brown solutions with DHN-β-D-glucuronide while catechol-β-D-glucuronide still gave greyish-black solutions. With either substrate, the colour of these solutions of mixed chromogens could be very readily distinguished with the unaided eye from the yellow colour of those strains, such as E. cloacae, that produced β-D-galactosidase only. Similarly, a combination of either of the novel substrates with ONPG was able to detect the β-D-glucuronidase activity of Shigella sonnei, an important pathogen that is generally positive for both β-D-glucuronidase and β-D-galactosidase. The above results clearly demonstrate the potential of the novel chromogenic glucuronides to be used in a liquid medium to detect E. coli and other β-D-glucuronidase producers, either on their own or in combination with other substrates (e.g. with ONPG). Although the strains tested were of clinical origin, it will be appreciated that the present invention may be used to screen samples from food, environmental sources and water.

The invention claimed is:

1. A method of detecting β-D-glucuronidase activity in a liquid medium comprising the steps of:
   a) contacting, in the liquid medium, a water soluble iron compound and a β-D-glucuronidase substrate represented by following formula I with a substance suspected of containing or producing a glucuronidase:

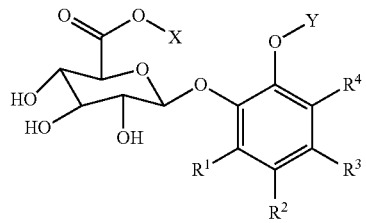

I wherein X is independently selected from the group consisting of H, $CH_3$, $C_2$-$C_6$ alkyl, a metal cation and a non-metal cation;
wherein Y is independently selected from the group consisting of H, a metal cation and a non-metal cation;
wherein either
   i) $R^1$ is H or OH and $R^4$ is H or $NO_2$; or
   ii) $R^1$ and $R^4$ are independently selected from the group consisting of H, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido; and
wherein $R^2$ and $R^3$ are independently selected from the group consisting of H, OH, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, sulfonyl and amido provided that $R^2$ and $R^3$ do not both represent OH, or $R^2$ and $R^3$ together form the group represented by formula VI:

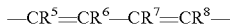

—$CR^5$=$CR^6$—$CR^7$=$CR^8$—    VI;

wherein $R^5$-$R^8$ are independently selected from the group consisting of H, $C_1$-$C_8$ alkyl, $C_1$-$C_8$ alkoxy, $C_1$-$C_8$ hydroxyalkyl, halogen, nitro, $C_2$-$C_{24}$ acyl, $C_2$-$C_{24}$ acyloxy, $C_7$-$C_{24}$ aralkyl, $C_6$-$C_{24}$ aryl, hydroxyl, sulfonyl and amido provided that in the formula VI any vicinal groups $R^5$ to $R^8$ are not both OH;
   such that a product of substrate cleavage is capable of chelating the iron compound, thereby forming a colored compound; and
   b) detecting presence of the colored compound.

2. The method according to claim 1 wherein the substrate is represented by formula II:

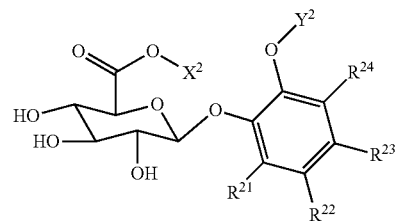

II wherein $X^2$ is independently selected from the group consisting of H, $CH_3$, $C_2$-$C_6$ alkyl, a metal cation and a non-metal cation;
wherein $Y^2$ is independently selected from the group consisting of H, a metal cation and a non-metal cation;
wherein $R^{21}$ is H or OH;
wherein $R^{24}$ is H or $NO_2$; and
wherein $R^{22}$ and $R^{23}$ are H or one of $R^{22}$ and $R^{23}$ is H and the other is OH, or $R^{22}$ and $R^{23}$ together form group VII:

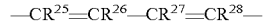

—$CR^{25}$=$CR^{26}$—$CR^{27}$=$CR^{28}$—    VII;

wherein $R^{25}$ to $R^{28}$ are independently selected from H, OH, $C_1$-$C_8$ alkyl, $C_1$-$C_8$ alkoxy, $C_1$-$C_8$ hydroxyalkyl, halogen, nitro, $C_2$-$C_{24}$ acyloxy, $C_7$-$C_{24}$ aralkyl, $C_6$-$C_{24}$ aryl, acyl, $C_2$-$C_{24}$ sulfonyl and amido, provided that any vicinal groups $R^{25}$-$R^{28}$ are not both OH.

3. The method according to claim 1, wherein the substance suspected of containing a β-D-glucuronidase is bacterial, wherein step a) of the method involves incubating the liquid medium in presence of the substrate, the iron compound and the substance.

4. The method according to claim 3, in which the bacteria are *Escherichia coli* or from the genera *Shigella* or *Salmonella*.

5. The method according to claim 1 in which the liquid medium contains at least one other enzyme substrate that is for a bacterial enzyme different from β-D-glucuronidase.

6. The method of claim 5 wherein the other enzyme substrate is a substrate for β-D-galactosidase, and the method includes the step of detecting the colored product of β-D-galactosidase cleavage.

7. The method according to claim 6 in which the other enzyme substrate is o-nitrophenyl-β-D-galactopyranoside.

8. The method according to claim 1, wherein the substance suspected of containing β-D-glucuronidase-producing microorganisms is water.

9. The method according to claim 1, wherein the iron compound is an iron salt of an organic or inorganic acid.

* * * * *